United States Patent [19]

Shirafuji et al.

[11] Patent Number: 4,876,195

[45] Date of Patent: Oct. 24, 1989

[54] PROCESS FOR PRODUCING 2-KETO-D-GLUCARIC ACID

[75] Inventors: Hideo Shirafuji, Nagaokakyo; Takamasa Yamaguchi, Suita; Ikuo Nogami, Nagaokakyo, all of Japan

[73] Assignee: Takeda Chemical Industries, Ltd., Osaka, Japan

[21] Appl. No.: 946,504

[22] Filed: Dec. 19, 1986

[30] Foreign Application Priority Data

Dec. 26, 1985 [JP] Japan .................. 60-294577

[51] Int. Cl.$^4$ .................. C07D 307/62; A23L 3/34
[52] U.S. Cl. .................. 435/137; 435/138; 435/822
[58] Field of Search .............. 435/137, 138, 143, 147, 435/148, 190, 822

[56] References Cited

U.S. PATENT DOCUMENTS 4,711,245 12/1987 Higgins et al. .................. 435/817

FOREIGN PATENT DOCUMENTS 222577 2/1984 Czechoslovakia .
228273 7/1987 European Pat. Off. .
0228273 8/1987 United Kingdom .............. 435/137

OTHER PUBLICATIONS

Kulhanek et al., Chemical Abstracts 101:22036X, 1984.

*Primary Examiner*—Ronald W. Griffin
*Assistant Examiner*—Pamela S. Webber
*Attorney, Agent, or Firm*—Wenderoth, Lind & Ponack

[57] ABSTRACT

2-Keto-D-glucaric acid is produced in high yield by contacting raw material saccharides (e.g. D-glucose) with a bacterium belonging to the genus Pseudogluconobacter or processed matters thereof.

8 Claims, 2 Drawing Sheets

PROCESS FOR PRODUCING 2-KETO-D-GLUCARIC ACID

The present invention relates to a process for producing 2-keto-D-glucaric acid (Formula 1) which works well as calcium-enriched additive for feed, detergent builder, cement plasticizer and reagent for saccharide metabolism study, by fermentation.

(I)

There is only one process for producing 2-keto-D-glucaric acid, in which *Pseudomonas aeruginosa* is allowed to act on D-glucaric acid synthesized from glucose by chemical oxidation to obtain 2-keto-D-glucaric acid via microbial oxidation (Czechoslovak Pat. No. 222577, Feb. 1, 1984).

The patented process above requires a process for synthesizing D-glucaric acid, the starting material, by chemical oxidation, and it is not thought of as a satisfactory industrial technique from the view point of yield.

While studying the mechanisms of microbial oxidation of monosaccharides, the present inventors found that a notable amount of 2-keto-D-glucaric acid is produced and accumulated in cultures obtained by culturing a bacterial strain (K591s, 12-5, 12-15, 12-4 or 22-3), isolated from soil samples, in a medium containing D-glucose, D-fructose and/or other monosaccharides as carbon sources. The inventors also made taxonomical studies on these bacteria and found that they were new bacterial strains belonging to a new genus, after which the present invention was developed as the result of further studies.

That is, the present invention provides a process for producing 2-keto-D-glucaric acid which comprises contacting a compound shown by the formula expressed as the chain structure (II)

wherein $R^1$ is —CHO, —CH$_2$OH or —COOH and $R^2$ is with a bacterium belonging to the genus Pseudogluconobacter and being capable of oxidizing the said compound or processed matters thereof, producing and accumulating 2-keto-D-glucaric acid and then recovering the same.

The strain K591s and the strains 12-5, 12-15, 12-4 and 22-3 were isolated from soil samples collected in Wakayama Prefecture and Shiga Prefecture, Japan, respectively. These 5 strains each have the following taxonomical characteristics:

TAXONOMIC CHARACTERISTICS OF STRAINS K591S AND 12-5

(a) Morphology
 (1) Rods, 0.3~0.5×0.7~1.4 μm in size.
 (2) Cell polymorphism not found.
 (3) Motile with 2~4 polar flagella.
 (4) Sporulation not found.
 (5) Gram-negative.
 (6) Not acid-fast.
(b) Growth states on various media
 (1) Nutrient agar plate culture: Hardly grows. When cultured on a yeast extract nutrient agar plate, forms a circular, entire, smooth, opalescent colony.
 (2) Yeast extract nutrient agar slant culture: Grows to a moderate degree. Shows a filiform, smooth, opalescent growth.
 (3) Yeast extract nutrient liquid culture: Grows to a moderate degree. Produces uniform turbidity throughout the medium.
 (4) Nutrient gelatin stab culture: Grows feebly only in the upper part. Gelatin liquefaction does not occur.
 (5) Litmus milk: Acidifies. Coagulates.
(c) Physiological characteristics
 (1) Positive in nitrate reduction, though weak.
 (2) Denitrification not found.
 (3) Positive in methyl red (MR) test.
 (4) Negative in Voges-Proskauer (VP) test.
 (5) Does not produce indole.
 (6) Does not produce hydrogen sulfide.
 (7) Does not hydrolyze starch.
 (8) Negative in citrate utilization.
 (9) Utilizes ammonium salts.
 (10) Chromogenicity not found.
 (11) Produces urease.
 (12) Positive in oxidase test.
 (13) Positive in catalase test.
 (14) Grows between 16° C. and 36° C. Optimum temperature is 24°~34° C. Grows between pH 5.5 and pH 8.7. Optimum pH is 6.0~7.5.
 (15) Aerobic.
 (16) Oxidative in Hugh-Leifson's OF test.
 (17) Acid but not gas from L-arabinose D-xylose, D-glucose, D-fructose, D-galactose, D-mannose, maltose, sucrose, lactose, trehalose, D-mannitol, and glycerol. Neither acid nor gas from D-sorbitol, inositol or starch.
(d) Other characteristics
 (1) Produces acetic acid from ethanol, though in a trace amount.
 (2) Depends on biotin, thiamine, riboflavin and coenzyme A (hereinafter also referred to as CoA) for growth.
 (3) Produces dihydroxyacetone from glycerol.
 (4) DNA has a guanine+cytosine content of 67±1 mole%.
 (5) Contains ubiquinone having 10 isoprene units (CoQ$_{10}$).
 (6) Resistant to streptomycin.

TAXONOMIC CHARACTERISTICS OF STRAIN 12-15

(a) Morphology
  (1) Rods, 0.3~0.5×0.7~1.4 μm in cell size.
  (2) Cell polymorphism not found.
  (3) Motile with 2~4 polar flagella.
  (4) Sporulation not found.
  (5) Gram-negative.
  (6) Not acid-fast.
(b) Growth states on various media
  (1) Nutrient agar plate culture: Hardly grows. When cultured on a yeast extract nutrient agar plate, forms a circular, entire, smooth, opalescent colony.
  (2) Yeast extract nutrient agar slant culture: Grows to a moderate degree. Shows a filiform, smooth, opalescent growth.
  (3) Yeast extract nutrient liquid culture: Grows to a moderate degree. Produces uniform turbidity throughout the medium.
  (4) Nutrient gelatin stab culture: grows feebly only in the upper part. Gelatin liquefaction does not occur.
  (5) Litmus milk: Acidifies but does not coagulate.
(c) Physiological characteristics
  (1) Negative in nitrate reduction.
  (2) Denitrification not found.
  (3) Positive in methyl red (MR) test.
  (4) Negative in Voges-Proskauer (VP) test.
  (5) Does not produce indole.
  (6) Does not produce hydrogen sulfide.
  (7) Does not hydrolyze starch.
  (8) Negative in citrate utilization.
  (9) Utilizes ammonium salts.
  (10) Chromogenicity not found.
  (11) Produces urease.
  (12) Positive in oxidase test.
  (13) Positive in catalase test.
  (14) Grows between 23° C. and 32° C., optimum temperature being 28°~32° C. Grows between pH 6.0 and pH 7.5. Optimum pH is 6.5~7.1.
  (15) Aerobic.
  (16) Oxidative in Hugh-Leifson's OF test.
  (17) Acid but not gas from L-arabinose, D-xylose, D-glucose, D-fructose, D-galactose, D-mannose, maltose, sucrose, lactose, trehalose and glycerol. Neither acid nor gas from D-mannitol, D-sorbitol, inositol or starch.
(d) Other characteristics
  (1) Produces acetic acid from ethanol, though in a trace amount.
  (2) Depends on biotin, thiamine, riboflavin and CoA for growth.
  (3) Produces dihydroxyacetone from glycerol.
  (4) DNA has a guanine+cytosine content of 67±1 mole%.
  (5) Contains ubiquinone having 10 isoprene units ($CoQ_{10}$).
  (6) Resistant to streptomycin.

TAXONOMIC CHARACTERISTICS OF STRAIN 12-4

(a) Morphology
  (1) Rods, 0.3~0.5×0.7~1.4 μm in cell size.
  (2) Cell polymorphism not found.
  (3) Motile with 2~4 polar flagella.
  (4) Sporulation not found.
  (5) Gram-negative.
  (6) Not acid-fast.
(b) Growth states on various media
  (1) Nutrient agar plate culture: Grows only in very small colony; full observation not possible. When cultured on a yeast extract nutrient agar plate, forms a circular, entire, smooth, opalescent colony.
  (2) Yeast extract nutrient agar slant culture: Grows to a moderate degree, showing a filiform, smooth, opalescent growth.
  (3) Yeast extract nutrient liquid culture: Grows to a moderate degree, producing uniform turbidity throughout the medium.
  (4) Nutrient gelatin stab culture: Grows feebly only in the upper part. Gelatin liquefaction does not occur.
  (5) Litmus milk: Acidifies but does not coagulate.
(c) Physiological characteristics
  (1) Negative in nitrate reduction.
  (2) Denitrification not found.
  (3) Positive in methyl red (MR) test.
  (4) Negative in Voges-Proskauer (VP) test.
  (5) Does not produce indole.
  (6) Produces hydrogen sulfide.
  (7) Does not hydrolyze starch.
  (8) Negative in citrate utilization.
  (9) Utilizes ammonium salts.
  (10) Chromogenicity not found.
  (11) Produces urease.
  (12) Positive in oxidase test.
  (13) Positive in catalase test.
  (14) Grows between 16° C. and 36° C., optimum temperature between 24°~34° C. Grows between pH 5.5 and pH 8.2. Optimum pH is 6.0~7.5.
  (15) Aerobic.
  (16) Oxidative in Hugh-Leifson's OF test.
  (17) Acid but not gas from L-arabinose, D-xylose, D-glucose, D-fructose, D-galactose, D-mannose, maltose, sucrose, lactose, trehalose and glycerol. Neither acid nor gas from D-mannitol, D-sorbitol, inositol or starch.
(d) Other characteristics
  (1) Produces acetic acid from ethanol, though in a trace amount.
  (2) Depends on biotin, thiamine, riboflavin and either CoA or pantothenic acid for growth.
  (3) Produces dihydroxyacetone from glycerol.
  (4) DNA has a guanine+cytosine content of 67±1 mole%.
  (5) Contains ubiquinone having 10 isoprene units ($CoQ_{10}$).
  (6) Resistant to streptomycin.

TAXONOMIC CHARACTERISTICS OF STRAIN 22-3

(a) Morphology
  (1) Rods, 0.3~0.5×0.7~1.4 μm in cell size.
  (2) Cell polymorphism not found.
  (3) Motile with 2~4 polar flagella.
  (4) Sporulation not found.
  (5) Gram-negative.
  (6) Not acid-fast.
(b) Growth states on various media
  (1) Nutrient agar plate culture: Grows only in very small colony; full observation not possible. When cultured on a yeast extract nutrient agar plate, forms a circular, entire, smooth, opalescent colony.
  (2) Yeast extract nutrient agar slant culture: Grows to a moderate degree, showing a filiform, smooth, opalescent growth.

(3) Yeast extract nutrient liquid culture: Grows to a moderate degree, producing uniform turbidity throughout the medium.
(4) Nutrient gelatin stab culture: Grows feebly only in the upper part. Gelatin liquefaction does not occur.
(5) Litmus milk: Acidifies but does not coagulate.
(c) Physiological characteristics
(1) Positive in nitrate reduction, though weak.
(2) Denitrification not found.
(3) Positive in methyl red (MR) test.
(4) Negative in Voges-Proskauer (VP) test.
(5) Does not produce indole.
(6) Does not produce hydrogen sulfide.
(7) Does not hydrolyze starch.
(8) Negative in citrate utilization.
(9) Utilizes ammonium salts.
(10) Chromogenicity not found.
(11) Produces urease.
(12) Positive in oxidase test.
(13) Positive in catalase test.
(14) Grows between 16° C. and 38° C., optimum temperature is 24°~34° C. Grows between pH 5.5 and pH 8.7. Optimum pH is 6.0~7.8.
(15) Aerobic.
(16) Oxidative in Hugh-Leifson's OF test.
(17) Acid but not gas from L-arabinose, D-xylose, D-glucose, D-fructose, D-galactose, D-mannose, maltose, sucrose, lactose, trehalose and glycerol. Neither acid nor gas from D-mannitol, D-sorbitol, inositol and starch.
(d) Other characteristics
(1) Produces acetic acid from ethanol, though in a trace amount.
(2) Depends on biotin, thiamine, riboflavin and either CoA or pantothenic acid for growth.
(3) Produces hydroxyacetone from glycerol.
(4) DNA has a guanine+cytosine content of 67±1 mole %.
(5) Contains ubiquinone having 10 isoprene units ($CoQ_{10}$).
(6) Resistant to streptomycin.

These 5 bacterial strains isolated from soil samples were each collected with the bacterial species described in Bergey's Manual of Determinative Bacteriology, 8th edition (1974) and Bergey's Manual of Systematic Bacteriology, Vol. 1 (1984); the 5 strains, i.e., Strains K591s, 12-5, 12-15, 12-4 and 22-3, appear initially to belong to the genus Pseudomonas because all are aerobic, Gram-negative, oxidase test-positive, motile bacilli having flagella. They resemble Pseudomonas diminuta and P. vesicularis in the points that they depend on growth factors, that the guanine+cytosine content of their DNA is 67±1 mole %, and that they contain ubiquinone having 10 isoprene units as the quinone system. However, these 5 strains differ from bacteria of the genus Pseudomonas in that they produce acetic acid from ethanol, though in a trace amount, and they they produce dihydroxyacetone from glycerol.

These characteristics are possessed by bacterial species of the genus Gluconobacter. However, these 5 strains differ from bacteria belonging to this genus in the points that they are positive in oxidase activity, that they cannot grow at pH 4.5, that they can grow completely on either yeast extract nutrient media containing no sugar (energy source) or peptone-yeast extract media, and that the guanine+cytosine content of their DNA is 67±1 mole%.

That is, none of these 5 strains, i.e., strains K591s, 12-5, 12-15, 12-4 and 22-3, belong to any known genera; they should be regarded as new bacterial species of a new genus. Strains K591s, 12-5, 12-15, 12-4 and 22-3 were thus named *Pseudogluconobacter saccharoketogenes*.

These bacterial strains are hereinafter referred to as oxidizing bacteria in some cases. Their nutritional requirements are described as follows: strains K591s, 12-5 and 12-15 have an uncommon nutritional requirement, i.e., they require CoA for growth. CoA cannot be replaced by panthothenic acid in these 3 strains. On the other hand, strains 12-4 and 22-3 can grow in the presence of CoA and/or pantothenic acid.

The bacterial strains which can be used in the present invention include not only those described above but also mutants obtained by irradiating these strains with UV or X-rays or by treating them with chemical mutagens such as N-methyl-N'-nitro-N-nitrosoguanidine (nitrosoguanidine), methyl methane-sulfonate or nitrogen mustard. These methods of obtaining mutants are conventional.

As an example of such mutants, there may be mentioned the strain TH14-86 which was derived from the strain K591s by treating it with nitrosoguanidine. This mutant strain TH14-86 exhibits the same taxonomical characteristics as the parent strain except that it shows an increased ability to produce 2-keto-D-gulcaric acid from raw material saccharides described below.

The above-mentioned *Pseudogluconobacter saccharoketogenes* K591s, 12-5 and TH 14-86 were deposited at the Institute for Fermentation, Osaka, (IFO) on Sept. 19, 1985 and *Pseudogluconobacter saccharoketogenes* 12-15, 12-4 and 22-3 on Dec. 16, 1985.

Furthermore, *Pseudogluconobacter saccharoketogenes* K591s, 12-5 and TH 14-86 were deposited at Fermentation Research Institute (FRI) of the Agency of Industrial Science and Technology, the Ministry of International Trade and Industry on Oct. 7, 1985 and *Pseudogluconobacter saccharoketogenes* 12-15, 12-4 and 22-3 on Dec. 20, 1985.

Based on the Budapest Treaty, these microorganisms have been kept at FRI since Aug. 9, 1986.

The deposit numbers at IFO and at FRI are as follows:

| Microorganism | IFO | FRI | |
|---|---|---|---|
| *Pseudogluconobacter saccharoketogenes* K591s | 14464 | P-8481 | BP-1130 |
| *Pseudogluconobacter saccharoketogenes* 12-15 | 14465 | P-8480 | BP-1129 |
| *Pseudogluconobacter saccharoketogenes* TH14-86 | 14466 | P-8479 | BP-1128 |
| *Pseudogluconobacter saccharoketogenes* 12-15 | 14482 | P-8577 | BP-1132 |
| *Pseudogluconobacter saccharoketogenes* 12-4 | 14483 | P-8756 | BP-1131 |
| *Pseudogluconobacter saccharoketogenes* 22-3 | 14484 | P-8578 | BP-1133 |

Compounds which can be used for the compound (II) in the present invention include D-glucose, D-fructose, D-mannose, D-sorbitol, D-mannitol, D-gluconic acid, 2-keto-D-gluconic acid, D-glucosone and D-mannoic acid. These compounds are hereinafter also referred to as "raw material saccharides".

Invert sugar made from sucrose or molasses by the action of invertase can also work well as a raw material saccharide.

In the present invention, it is possible both to culture said bacteria in a medium containing raw material saccharides and to make processed bacterial cells act on raw material saccharides. "Processed bacterial cells" used in the present invention represent the preparation that contains enzyme system which is related to the reaction in which the raw material saccharide is oxidized, resulting in the formation of 2-keto-D-glucaric acid. To exemplify the said preparation, they are washed bacterial cells, dried bacterial cells, entrapped bacterial cells, or the like, which are obtained by having the said culture subjected to adequate treatment, e.q., centrifugal isolation, filtration, washing with solvent (e.g., saline), drying with acetone and dry ice, entrapping in either polyacrylamide gel or K-carrageenin, etc.

Raw material saccharides can be added to the medium either at the beginning of culturing, in several portions over time, or continuously during culturing.

When a reaction is sought by placing the said bacteria in contact with raw material saccharides, the saccharide concentration in the reaction liquid should be 1~30% (w/v) based on the medium, preferably 5~20% (w/v).

Raw material saccharides can be brought into contact with processed bacterial cells as follows: for example, to processed bacterial cells add raw material saccharides, a 2-(N-morpholino)-ethanesulfonic acid (MES) buffer solution (pH 6.5, 0.5M), and $CaCO_3$, dilute with water, and shake in a conical flask.

When a reaction is carried out by bringing said processed bacterial cells in contact with raw material saccharides, the saccharide concentration in the reaction liquid should be 0.1~10% (w/v) based on the medium. The quantity of processed bacterial cells should be 1~30 mg/ml, calculated on an unprocessed dry cell basis. The reaction liquid should be adjusted to a pH of approx. 5.5~7.5. Reaction temperature and reaction time can be chosen in the range of approx. 20°~40° C. and of approx. 1~100 hours.

Culture media for the bacteria described above can be either liquid or solid, as long as they contain nutrient sources which can be utilized by the said bacterial strains; however, it is recommended that a liquid medium is used for mass culture.

Additives which can be used for the said media include carbon sources, nitrogen sources, minerals, organic acid salts and trace nutrients used commonly for microbe culture.

The raw material saccharides described above can be used as carbon sources without any treatment; glycerol, sucrose, lactose, maltose, molasses etc. can be used as auxiliary carbon sources.

Substances which can be used as nitrogen sources include organic or inorganic nitrogen compounds such as ammonium salts (ammonium sulfate, ammonium nitrate, ammonium chloride, ammonium phosphate, etc.), corn steep liquor (hereinafter referred to as CSL in some cases), peptone, meat extract, yeast extract, dry yeast, soybean meal, cotton seed flour and urea. Minerals which can be used include salts of potassium, sodium, calcium, magnesium, iron, manganese, cobalt, zinc, copper, or phosphates.

Trace nutrients which can be used include not only the nutritional factors essential to the growth of the bacteria described above, i.e., CoA, pantothenic acid, biotin, thiamine, and riboflavin, but also those compounds having a promoting effect on their growth and 2-keto-D-glucaric acid production, such as flavin mononucleotide (hereinafter also referred to as FMN), flavin adenine dinucleotide (hereinafter also referred to as FAD), other vitamins, L-cysteine, L-glutamic acid and sodium thiosulfate in the form either of chemical compounds or natural substances containing them.

Culturing methods which can be used include standing culture, shaking culture and submerged culture. With mass culture, what is called submerged culture is recommended.

Culturing conditions depend on the bacterial strain, medium composition, and other factors; the conditions can be chosen according to the requirements of each case so that the desired product is produced at the highest efficiency. For example, it is recommended that culturing temperature is 25°~35° C., and the pH of the medium is 5~9. 2-Keto-D-glucaric acid can be accumulated to the maximum concentration by carrying out either culture or reaction for 10~120 hours under the conditions shown above. In this case, pH level usually decreases as the desired product is produced; it is therefore recommended that either a suitable basic substance such as sodium hydroxide, potassium hydroxide or ammonia, or a suitable buffer be added to the medium to maintain the optimum pH for producing 2-keto-D-glucaric acid.

Sterilized cultures of bacterial species other than the oxidizing bacteria described previously can also work well as components of the medium. Bacteria which can be used for this purpose include those of the genera Bacillus, Pesudomonas, Citrobacter, Escherichia, and Erwinia. Specifically, the following bacteria can be used:

*Bacillus cereus* IFO 3131
*Bacillus subtilis* IFO 3023
*Bacillus pumilus* IFO 12089
*Bacillus megaterium* IFO 12108
*Bacillus amyloliquefaciens* IFO 3022
*Pseudomonas trifolii* IFO 12056
*Citrobacter freundii* IFO 12681
*Escherichia coli* IFO 3546
*Erwinia herbicola* IFO 12686

It is possible to promote the growth of oxidizing bacteria in the following manner: culture these other bacteria in a suitable medium at 20°~40° C. for 2 to 4 days and after sterilization, add the resulting culture broth to the medium for the oxidizing bacteria at a ratio of 0.5~5.0% (v/v).

2-Keto-D-glucaric acid produced and accumulated either in the culture broth or in the reaction liquid as above can be separated and purified by conventional methods based on its properties. 2-Keto-D-glucaric acid can be separated in the form either of a free acid or of a salt of sodium, potassium, calcium, ammonium etc.

Any separation method can be employed, as long as it does not interfere with the objective. For example, bacterial cells are previously removed from the reaction product by filtration or centrifugation and decoloration can be performed by activated charcoal treatment etc., if necessary. The solution of the reaction product is then concentrated to precipitate crystals. The resulting crystals are collected via filtration and recrystallized to separate the desired product. Solvent extraction, chromatography, salting-out etc. can also be used, either singly or in combination, and either at one time or repeatedly.

When 2-keto-D-glucaric acid is obtained in the form of a free acid, it can be converted to a salt of sodium, potassium, calcium, ammonium etc. by a suitable method; when it is obtained in the form of a salt, it can be converted to either a free acid or another salt by a suitable method.

The desired product obtained by the present invention was identified as 2-keto-D-glucaric acid by determining its physicochemical properties, such as elemental composition, melting point, optical rotation and infrared spectrum.

2-Keto-D-glucaric acid, produced in either the reaction liquid or the culture broth, was quantitatively analyzed via high performance liquid chromatography (mobile phase: diluted sulfuric acid, pH 2.2; flow rate: 0.5 ml/min.; detector: differential refractometer) using a column packed with sulfonated polystyrene gel (Shimadzu Corp., SCR-101H column, 7.9 mm×30 cm); 2-keto-D-glucaric acid prepared from D-glucaric acid using *Pseudomonas aeruginosa* (IFO 3448) in accordance with Czechoslovak Pat. No. 222,577 (1984) of Kulhanek Milos et al. was used as the standard sample, as described in the reference example mentioned below.

Using bacteria of the genus Pseudogluconobacter capable of oxidizing D-glucose etc. to 2-keto-D-glucaric acid, the present invention makes it possible to produce 2-keto-D-glucaric acid at a high yield.

The present invention is hereinafter described in more detail with one reference example and some examples. Unless otherwise specified, % values for media are shown in weight/volume% (w/v%).

REFERENCE EXAMPLE 30 ml of a medium composed of 0.5% peptone, 0.5% yeast extract, 1.0% D-glucose, and 0.1% $K_2HPO_4$ (hereinafter also referred to as PYG medium) was transferred to a 200 ml conical flask and autoclaved at 120° C. for 20 minutes. To this flask was inoculated one loopful of fresh cells of *Pseudomonas aeruginosa* (IFO3448) grown at 28° C. for 2 days on a slant medium prepared by adding 2.0% agar to a PYG medium. The bacterial cells were then subjected to rotary shaking culture (200 rpm) at 30° C. for 24 hours; the resulting culture broth was used as the seed culture broth.

A 5% (w/v) aqueous solution of monopotassium D-glucaric acid (Sigma Corp., USA), previously adjusted to pH 7.0 with NaOH, was subjected to filtration through a 0.45-μ pore size filter to remove microbes, after which it was added to a PYG medium to a concentration of 1% (w/v). One ml of the seed culture broth described above was transplanted to a 200 ml-conical flask containing 20 ml of this medium and subjected to shaking culture at 30° C. for 24 horus. The resulting culture broth was found via high performance liquid chromatography to contain 9.02 mg/ml 2-keto-D-glucaric acid. The culture broth (590 ml) was centrifuged to remove bacterial cells, yielding 580 ml supernatant. The resulting supernatant was passed through a column packed with Amberlite cation exchange resin IR 120B (H+ form, Roam & Haas Co., USA, 200 ml), after which the column was washed with 150 ml deionized water to remove cations. The supernatant was then passed through a column packed with activated charcoal (70 ml), the column being washed with 50 ml deionized water to decolor the supernatant. The effluent (780 ml) was then adjusted to pH 6.5 with $Ca(OH)_2$; after removal of white turbidity by filtration, it was concentrated to approx. 20 ml under reduced pressure.

White amorphous crystals formed in the concentrate were collected on a glass filter, washed with a series of small amounts of cold water, methanol, and ethyl ether, and dried under reduced pressure to yield 5.04 g 3.5-hydrated dicalcium 2-keto-D-glucarate. The analytical data for this crystalline substance are as follows:

Melting point: 152°~157° C. (decomposition)

Elemental analysis data ($C_6H_6O_8Ca.3.5H_2O$) (%): Calculated: C; 23.30, H; 4.24, Ca; 12.96. Found: C; 23.15, H; 4.18, Ca; 14.00.

Specific optical rotation: $[\alpha]_D^{25} = +9.0°$ (c=1.075, 0.1N HCl).

IR absorption spectrum: Main absorption wavenumbers are as follows:

Wavenumber ($cm^{-1}$) 3590, 3500, 3400~2700 (br)*, 1650, 1600, 1430, 1380, 1360, 1300, 1250, 1240, 1220, 1125, 1095, 1065, 1040, 1005, 995, 955, 900, 840, 800, 765, 725

(*) br: broad

EXAMPLE 1

Twenty ml of a seed medium composed of 2.0% D-glucose, 1.0% peptone, 1.0% dry yeast, and 2.0% $CaCO_3$ was transferred to a 200 ml-conical flask and autoclaved at 120° C. for 20 minutes. To this flask was inoculated one loopful of cells of *Pseudogluconobacter saccharoketogenes* K591s (FERM BP-1130, IFO 14464) grown at 28° C. for 4 days on a slant medium composed of 2.5% D-sorbitol, 1.0% peptone, 1.0% yeast extract, 0.2% $CaCO_3$, and 2.0% agar, followed by shaking culture (200 rpm) at 30° C. for 2 days to yield the seed culture broth. Separately, 200 ml of a medium whose composition was the same as that of the seed medium was transferred to a 1 l-conical flask and sterilized in the same manner as above, after which 10 ml of the seed culture broth was transplanted to this flask and then subjected to shaking culture at 30° C. for 3 days.

The resulting culture broth was found to contain 19.4 mg/ml 2-keto-D-glucaric acid.

This culture broth (1600 ml) was centrifuged (7000 rpm, 10 minutes) to remove the precipitate containing bacterial cells, yielding 1520 ml supernatant. After cooling to 4° C., the resulting supernatant was left to stand for 3 days, yielding amorphous crystals of calcium 2-keto-D-glucarate. The resulting crystals were collected on a glass filter (No. 3), washed with a series of small amounts of cold water, methanol, and ethyl ether, and dried on phosphorus pentoxide under reduced pressure: 18 g trihydrated dicalcium 2-keto-D-glucarate was obtained. The analytical data for the resulting crystalline substance are as follows: Melting point: 152°~157° C. (decomposition)

Elemental analysis data ($C_6H_6O_8Ca.3H_2O$) (%): Calculated: C; 24.00, H; 4.03, Ca; 13.35 Found: C; 23.96, H; 4.16, Ca; 13.00

Specific optical rotation: $[\alpha]_D^{25} = +7.9°$ (c=1.065, 0.1N HCl).

IR absorption spectrum: Main absorption wavenumbers are as follows:

Wavenumber ($cm^{-1}$) 3590, 3500, 3400~2700 (br)*, 1650, 1600, 1430, 1380, 1360, 1300, 1250, 1240, 1220, 1125, 1095, 1065, 1040, 1005, 995, 955, 900, 840, 800, 765, 725

(*) br: broad

Figure 1:
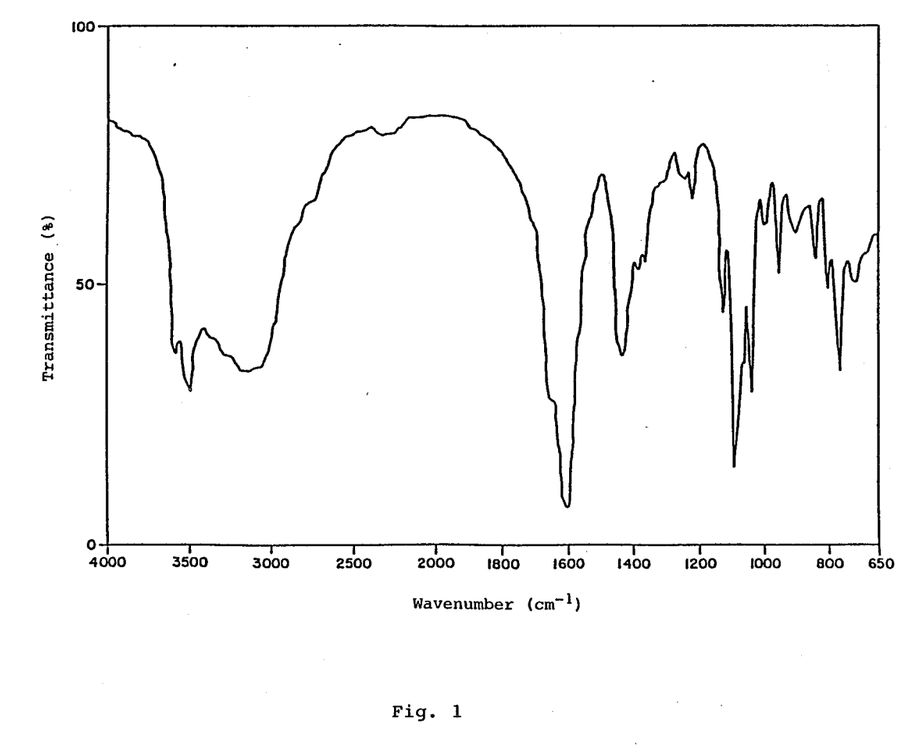
FIGS. 1 and 2 show the infrared absorption spectra of the crystalline substances obtained in Example 1 and of the standard sample obtained in Reference Example, respectively.
Figure 2:
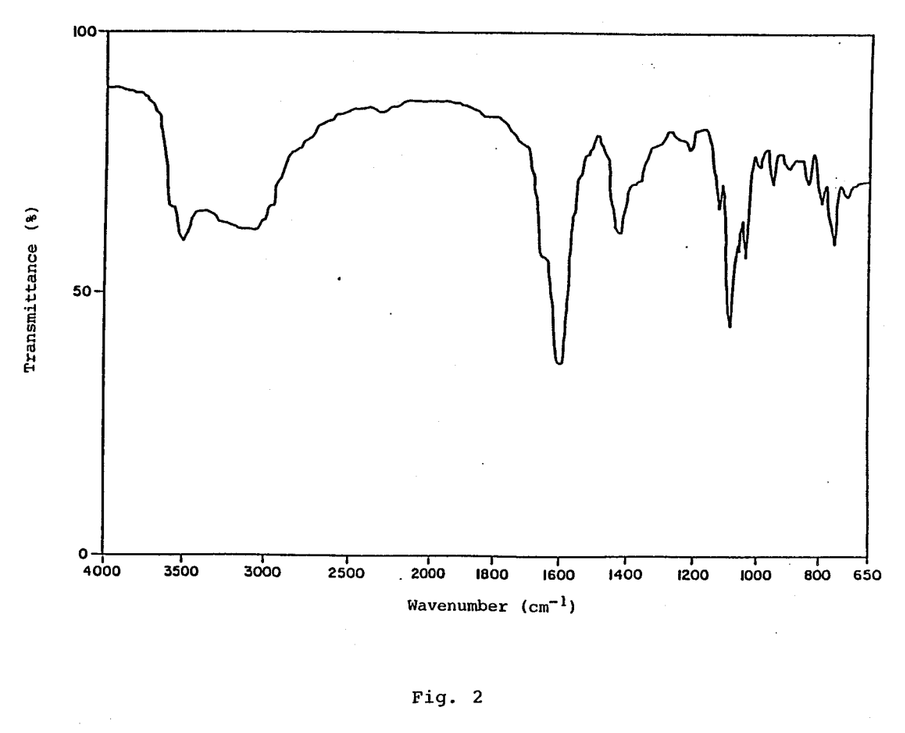

This crystalline substance and the standard sample exhibited the same IR spectrum (FIGS. 1 and 2 respectively), the same retention time (9.4 minutes) in high performance liquid chromatography and the same ratio of UV absorption at 214 nm to differential refraction index (approx. 1.0). The crystalline substance and the standard sample were subjected, at room temperature for 3 hours, to thin-layer chromatography using both a cellulose plate (Merck) and a mixture of phenol, formic acid and water (75:5:25) as solvent; exhibited the same Rf value (0.20). Moreover, both were the same in coloration reactions, i.e., both changed in color to blackish-brown, yellow, and yellow in reaction to silver nitrate reagent, o-phenylene diamine reagent, and anilinephthalic acid reagent, respectively.

Based on the analytical data shown above, the glucose metabolite produced by *Pseudogluconobacter saccharoketogenes* K 591s was identified as 2-keto-D-glucaric acid.

EXAMPLE 2

Using the same method as shown in Example 1, seed culture broth of *Pseudogluconobacter saccharotogenes* strains K591s (FERM BP-1130, IFO 14464), 12-5 (FERM BP-1129, IFO 14465), 12-15 (FERM BP-1132, IFO 14482), 12-4 (FERM BP-1131, IFO 14483) and 22-3 (FERM BP-1133, IFO 14484) were prepared. A fermentation medium was prepared by adding the raw material saccharides at a concentration of 5% (w/v) (shown in Table 1), previously sterilized, to a medium (pH 6.5) composed of 3.0% CSL, 0.5% dry yeast, 0.5% ammonium sulfate, 0.05% sodium thiosulfate, 0.2% ferric sulfate and 3.0% $CaCO_3$. 1.25 ml of each seed culture broth was transplanted to a 200 ml-conical flask containing 25 ml of this fermentation medium and subjected to shaking culture at 30° C. for 3 days. The resulting culture broth was diluted with 0.3N sufuric acid and centrifuged, after which the resulting supernatant was subjected to high performance liquid chromatography to determine the 2-keto-D-glucaric acid content. The results of the determination are shown in Table 1.

TABLE 1

Production Quantities for 2-Keto-D-glucaric Acid (mg/ml)

| Raw Material Saccharide (5%) | Bacterial Strain | | | | |
|---|---|---|---|---|---|
| | K591S | 12-5 | 12-15 | 12-4 | 22-3 |
| D-glucose | 44.9 | 49.1 | 57.1 | 41.6 | 48.6 |
| D-fructose | 33.0 | 40.3 | 39.4 | 20.8 | 42.7 |
| D-sorbitol | 14.6 | 31.5 | 16.5 | 14.9 | 42.4 |
| D-mannose | 4.9 | 5.2 | 8.8 | 15.8 | 9.5 |
| D-mannitol | 8.2 | 12.6 | 10.3 | 7.7 | 15.1 |
| D-gluconic acid | 31.8 | 33.1 | 18.2 | 9.5 | — |
| 2-keto-D-gluconic acid* | 16.4 | 19.7 | 13.5 | 5.3 | — |

*This was used at a concentration of 2.5% (w/v).

EXAMPLE 3

The preculture medium (500 ml) composed of 2.0% D-glucose, 1.0% peptone, 1.0% dry yeast, 2.0% calcium carbonate, and 0.01% Actcol (antifoaming agent, Takeda Chemical Industries) was transferred to a 2 l-Sakaguchi flask and autoclaved at 120° C. for 20 minutes. Bacterial cells of *Pseudogluconobacter saccharoketogenes* strain 12-5 (FERM BP-1129, IFO 14465), grown at 28° C. for 4 days on the slant medium shown in Example 1, were suspended in 10 ml sterile water and the entire suspension was transplanted to the before-mentioned Sakaguchi flask, after which it was subjected to reciprocal shaking culture (85 spm) at 28° C. for 2 days to yield a culture broth for used as preculture.

Thirty liters of a seed culture medium composed of 3.0% D-glucose, 1.0% peptone, 1.0% dry yeast, 2.0% calcium carbonate, and 0.03% Actcol was fed to a 50 l-fermentor and autoclaved at 125° C. for 20 minutes. One liter of the preculture broth described above was transplanted to this fermentor and cultured at 28° C. and 1.0 $Kg/cm^2G$ under aeration at 24 l/min. for 2 days while stirring at 200 rpm to yield a seed culture broth.

Separately, bacterial cells of *Bacillus megaterium* (IFO 12108), grown at 28° C. for 2 days on the slant medium shown in Example 1, were suspended in 10 ml sterile water and the entire suspension was inoculated to a sakaguchi flask containing the same preculture medium, after which it was subjected to reciprocal shaking culture (84 spm) at 28° C. for 2 days to yield a seed culture broth of *Bacillus megaterium*.

Thirty liters of a medium (pH 7.0) composed of 4.0% sucrose, 4.0% cotton seed flour, 0.65% $K_2HPO_4$, 0.55% $KH_2PO_4$, 0.05% ammonium sulfate, 0.05% NaCl, 0.05% magnesium sulfate and 0.05% calcium pantothenate was fed in a 50 l-fermentor and autoclaved at 125° C. for 20 minutes. One liter of the seed culture broth of *Bacillus megaterium* was transplanted to this fermentor and cultured at 28° C. and 1.0 $Kg/cm^2G$ inside pressure under aeration at 24 l/min. for 4 days while stirring at 200 rpm. The resulting culture broth was autoclaved with steam at 120° C. for 20 minutes, stored in a cool place and use as the sterilized culture broth of *Bacillus megaterium* for a component of the following fermentation medium.

To a 200 l-fermentor was fed 120 l of a fermentation medium composed of 10.0% D-glucose (separately sterilized at 120° C. for 15 minutes), 1.0% peptone, 0.1% ferrous sulfate, 0.01% L-cysteine, 6.0% calcium carbonate, 1 $\mu g/ml$ FMN, 1 $\mu g/ml$ thiamine hydrochloride, 0.5 $\mu g/ml$ biotin, 0.02% Actcol, and 4.0% of the before-mentioned sterilized culture broth of *Bacillus megaterium*, after which it was autoclaved at 125° C. for 20 minutes. Ten liters of the seed culture broth described above was transplanted to this fermentor and cultured at 28° C. and 1.0 $Kg/cm^2G$ under aeration at 96 l/min. for 4 days while stirring at 200 rpm. The resulting culture broth was found to contain 99.3 mg/ml 2-keto-D-glucaric acid.

This culture broth (110 l), treated using a Sharpless centrifuge (15,000 rpm), yielded approx. 31 kg wet precipitate. This wet precipitate was washed with 150 l water, centrifuged (3,000 rpm), after which it was suspended in 30 l acetone, dehydrated and centrifuged (3,000 rpm), yielding a white powder which was then dried at 50° C. under reduced pressure for 24 hours, yielding 14.6 kg white, crude powder of dicalcium 2-keto-D-glucarate. The purity of this crude powder was 58.9%, calculated on the basis of free 2-keto-D-glucaric acid.

EXAMPLE 4

Five grams of the crude dicalcium 2-keto-D-glucarate obtained in the same manner as in Example 1 [containing 85.1% trihydrated dicalcium 2-keto-D-glucarate ($C_6H_6O_8Ca.3H_2O$), as found in quantitative determination by high performance liquid chromatography*] was placed in a 500 ml-Erlenmeyer flask and suspended in 300 ml distilled water while stirring. Sixty ml cation exchange resin IR-120B (Rohm & Haas Co., USA) was added to this suspension and stirred at room temperature for 1 hour. The reaction product was passed through a glass filter; the residual solid was washed with 100 ml distilled water. The filtrate and washings were combined and concentrated to approx. 50 ml under reduced pressure. The resulting concentrate was then subjected to fine filtration through a Millipore filter paper (Millipore Co., USA, GS WPO 4700, 0.22 μm in pore size) over which approx. 10 g Hyflo Super Cell (Johns Manville, USA, Cellite) was previously spread and washed with 20 ml distilled water, after which the washings were combined with the filtrate. The filtrate was found to contain 2.66 g 2-keto-D-glucaric acid under quantitative determination by high performance liquid chromatography (recovery: 90.1%).

This filtrate was then passed through a column packed with 10 g activated charcoal (Takeda Chemical Industries, Shirasagi A for chromatography) and washed with 100 ml distilled water. The effluent was divided and transferred to two 500 ml eggplant-shaped flasks and the water was evaporated by freeze-drying for 7 hours. The resulting colorless, oily substance was dried in the presence of phosphorus pentoxide under reduced pressure for 3 hours and used as the sample for elemental analysis and IR spectrometry.

Elemental analysis data (%) ($C_6H_8O_8.1.4H_2O$): Calculated: C; 30.88, H; 4.66. Found: C; 31.12, H; 4.57.

High performance liquid chromatography*: Retention time = 7.30 min.

(*) Measuring conditions for high performance liquid chromatography:
Instrument: Shimadzu LC-3A model
Column: Aminex ion exclusion HPX-87H, 300×7.8 mm (Bio-Rad)
Flow rate: 0.6 ml/min.
Column temperature: 25° C.
Mobile phase: 0.008N $H_2SO_4$
Detector: UV (210 nm) and RI (Showa Denko, SE-31 model).

IR (film): Main absorption wavenumbers (cm$^{-1}$) 3700~2700, 1730, 1700 (sh), 1680 (sh), 1640.

EXAMPLE 5

Ten ml 2-keto-D-glucaric acid solution [containing 2.71 g (0.013 mole) 2-keto-D-glucaric acid, as found in quantitative determination via high performance liquid chromatography; yield: 92.0%], prepared from 5.0 g crude trihydrated dicalcium 2-keto-D-glucarate [containing 85.1% $C_6H_6O_8Ca.3H_2O$] in accordance with the method shown in Example 4, was passed through a column packed with 30 ml Dowex 50W-X8 (cation exchange resin made by Dow Chemical Co., USA, Na+ form). The column was then subjected to elution with distilled water, yielding 400 ml effluent (exhibiting a pH value of 3.4). This effluent was then concentrated to dryness under reduced pressure. Methanol (400 ml) was added to the residue and stirred, yielding a powdery substance. The powder was then collected by filtration, washed with a small amount of acetone and dried in a desiccator under reduced pressure: 2.44 g monosodium 2-keto-D-glucarate was obtained (yield: 75.6%).

Melting point: 155°~160° C. (decomposition)

Elemental analysis data (%) ($C_6H_7O_8Na.H_2O$) Calculated: C; 29.04, H; 3.66. Found: C; 28.72, H; 3.80.

IR (KBr): Main absorption wavenumbers (cm$^{-1}$) 3600~2800, 1720, 1620, 1410.

EXAMPLE 6

Ten ml 2-keto-D-glucaric acid solution [containing 2.71 g (0.013 mole) 2-keto-D-glucaric acid, as found in quantitative determination by high performance liquid chromatography], prepared from 5.0 g crude trihydrated dicalcium 2-keto-D-glucarate (containing 85.1% $C_6H_6O_8Ca.3H_2O$) in accordance with the method described in Example 4, was passed through a column packed with 30 ml Dowex 50W-X8 (K+ form). The column was then subjected to elution with distilled water, yielding 400 ml effluent (exhibiting a pH value of 3.42). This effluent was then concentrated under reduced pressure and 400 ml methanol was added to the residue and stirred, yielding a powdery substance. This powder was collected by filtration, washed with a small amount of acetone, and dried in a desiccator under reduced pressure: 2.12 g monopotassium 2-keto-D-glucarate was obtained (yield: 61.7%).

Melting point: 135°~150° C. (decomposition).

Elemental analysis data (%) ($C_6H_7O_8K.H_2O$): Calculated: C; 27.27, H; 3.43. Found: C; 26.83, H; 3.66.

IR (KBr): Main absorption wavenumbers (cm$^{-1}$) 3600~2800, 1720, 1610, 1410.

EXAMPLE 7

TABLE 2

| Slant medium (g/l) | |
|---|---|
| D-Sorbitol | 25 |
| Peptone | 10 |
| Yeast extract | 10 |
| $CaCO_3$ | 2 |
| Agar | 20 |
| pH 7.0 | |

TABLE 3

| Complete medium (g/l) | |
|---|---|
| D-Sorbitol | 25 |
| Peptone | 10 |
| Yeast extract | 10 |
| pH 6.5 (In the case of a solid medium, 20 g of agar was added) | |

TABLE 4

| Minimum essential medium (g/l) | |
|---|---|
| Sucrose | 5 |
| $K_2HPO_4$ | 3 |
| $KH_2PO_4$ | 1 |
| $(NH_4)SO_4$ | 1 |
| NaCl | 1 |
| $MgSO_4.7H_2O$ | 0.1 |
| $MnCl_2.nH_2O$ | 0.002 |
| Sodium L-glutamate | 0.1 |
| L-cysteine | 0.1 |
| CoA | 0.002 |
| FMN | 0.002 |
| Thiamine | 0.002 |
| Biotin | 0.001 |
| pH 7.0 (In the case of a solid medium, 20 g of agar was added) | |

A test tube (16 mm×160 mm) containing 5 ml of a complete medium in Table 3 was inoculated with a loopful of *Pseudogluconobacter saccharoketogenes* K591s grown on a slant medium in Table 2 and cultured at 30° C. with shaking for 2 days. This culture broth (1 ml) was transferred to a test tube containing 5 ml of the same medium, which was then cultured with shaking for 4 hours. The resulting broth (5 ml) was aseptically centrifuged (12,000 r.p.m.) at 5° C. for 15 minutes to harvest the cells. The cells were suspended in 10 ml of tris-maleic acid buffer (pH 6.5; 0.05M) and recentrifuged. The above procedure was repeated twice and the washed cells were suspended in 5 ml of the abovementioned buffer containing 1 mg/ml of nitrosuguanidine and shaken at 30° C. for 2 hours for mutagenic treatment. The suspension was centrifuged (12,000 r.p.m.) at 5° C. for 15 minutes to collect the cells which were then washed twice with 10 ml portions of tris-maleic acid buffer to recover a fraction containing nitrosoguanidine-treated cells. This was diluted with 0.85% saline to a suitable concentration and spread over a plate (diameter: 9 cm) containing 15 ml of the complete medium (solid). The inoculated plate medium was cultured at 28° C. for 5 days to grow colonies. The colonies were counted and compared with the untreated control. The mortality of the microorganisms due to the nitrosoguanidine treatment was 90.4%. The colonies on the complete medium plate were replicated onto the minimum essential medium plates in Table 4 and after culturing at 28° C. for 3 days, the frequency of auxotrophs (nutritional mutants) was investigated. The frequency was about 6.6%.

The colonies treated with the mutagen on the complete medium plate were streaked onto a fresh complete medium plate over a length of about 2 cm at the rate of 12 strains per plate. After culturing at 28° C. for 2 days, one loopful of the grown cells were transferred to a test tube containing 3 ml of a medium (pH 6.5) composed of 7.0% D-glucose (separately sterilized), 1.0% dry yeast, 1.0% peptone, 0.1% ferrous chloride and 3.0% CaCO$_3$ and cultured with shaking at 30° C. for 3 days. Among the tested mutant strains, the strain TH14-86 was found to produce 2-keto-D-glucaric acid twice as much as the parental strain K591s under the above conditions. This strain TH14-86 (IFO 14466; FERM BP-1128) was chosen as an oxidative strain with an augmented ability to oxidize D-glucose.

EXAMPLE 8

The mutant strain TH14-86 derived from *Pseudogluconobacter saccharoketogenes* K591s in Example 7 was grown on a slant medium at 28° C. for 4 days. A loopful of the cells were taken from the slant culture and inoculated into a 200-ml conical flask containing 20 ml of the seed culture medium described in Example 1 and cultured at 30° C. with shaking for 2 days.

A conical flask of 1 liter capacity was charged with 200 ml of a preculture medium composed of 3.0% D-glucose, 1.0% peptone, 1.0% dry yeast and 2.0% CaCO$_3$ and sterilized by autoclaving at 120° C. for 20 minutes. This conical flask was inoculated with 20 ml of the above culture broth and cultured at 30° C. with shaking for 2 days to give a preculture broth of the strain TH 14-86.

A 5 l-jar fermentor was autoclaved and then charged with 2.4 l of a fermentation medium composed of 5.0% D-glucose (separately sterilized), 4.0% (v/v) sterilized culture broth of *Bacillus megaterium* (prepared in Example 3), 1.0% peptone, 0.3% ammonium sulfate, 0.05% Na$_2$S$_2$O$_3$, 0.03% KH$_2$PO$_4$, 0.05% magnesium sulfate, 0.1% FeSO$_4$.7H$_2$O, 0.05% Actcol, 5 mg/l MnSO$_4$.4H$_2$O, 1 mg/l FMN, 1 mg/l thiamine, 0.5 mg/l biotin and 9.0% CaCO$_3$, after sterilization by autoclaving at 120° C. for 30 minutes.

This fermentation medium was inoculated with 300 ml of the above preculture broth of the strain TH 14-86 and cultured at 32° C. with aeration at 2.0 l/min. and stirring at 800 r.p.m. for 54 hours, while 600 ml of D-glucose solution which was obtained by dissolving 300 g D-glucose in water and then autoclaving at 120° C. for 20 minutes was continuously added to the jarfermentor over 18 hours after culturing for the first 6 hours.

The resulting culture broth (3.05 l) was found to contain 164.9 mg/ml 2-keto-D-glucaric acid.

EXAMPLE 9

A 200-ml conical flask was charged with 25 ml of a medium (pH 7.0) composed of 1.0% L-sorbose (separately sterilized), 0.5% peptone, and 0.5% yeast extract and sterilized by autoclaving at 120° C. for 15 minutes. The flask was inoculated with a loopful of *Pseudogluconobacter saccharoketogenes* TH14-86 grown on a slant medium in Table 2 at 28° C. for 4 days and cultured at 30° C. with shaking for 2 days to give a seed culture.

A 200-ml conical flask was charged with 25 ml of a medium (pH 7.0) composed of 0.5% D-glucose (separately sterilized), 1.0% peptone, 0.5% yeast extract and 2.0% CaCO$_3$ and sterilized by autoclaving at 120° C. for 15 minutes. This flask was inoculated with 1.0 ml of the above seed culture and cultured at 30° C. for 2 days.

The resulting culture (460 ml) was allowed to stand at room temperature for 20 minutes and the sediment was removed by decantation. The remaining fluid was centrifuged at a slow speed of 1,000 r.p.m. at room temperature to remove the sediment composed predominantly of CaCO$_3$. The cell suspension thus obtained was further centrifuged (6,000 r.p.m.) at 5° C. for 10 minutes and the cells collected were washed twice with about 100 ml portions of cold saline (0.85%) and re-centrifuged (6,000 r.p.m.) at 5° C. to give washed cells. The cells were further suspended in 35 ml of cold saline (0.85%) to give a washed cell suspension. To 2 ml of this washed cell suspension were added 300 mg D-glucose, 0.5 ml 2-(N-morpholino)ethanesulfonic acid (MES) buffer (pH 6.5; 0.5M) and 180 mg of CaCO$_3$, followed by dilution with water to make 10 ml. The mixture was reacted in a 100-ml conical flask at 30° C. with shaking for 24 hours. The reaction mixture obtained in this manner was found to contain 25.7 mg/ml of 2-keto-D-glucaric acid.

What we claim is:

1. A process for producing 2-keto-D-glucaric acid which comprises contacting a compound shown by the formula expressed as the chain structure wherein R$^1$ is —CHO, —CH$_2$OH or COOH and R$^2$ is with a bacterium belonging to the genus Pseudogluconobacter and being capable of oxidizing said compound, or processed matters thereof in a medium, producing and accumulating 2-keto-D-glucaric acid and then recovering the same.

2. A process according to claim 1, wherein the bacterium is *Pseudogluconobacter saccharoketogenes*.

3. A process according to claim 1, wherein the bacterium is *Pseudogluconobacter saccharoketogenes* K591s (FERM BP-1130, IFO 14464), 12-5 (FERM BP-1129, IFO 14465), TH14-86 (FERM BP-1128, IFO 14466), 12-15 (FERM BP-1132, IFO 14482), 12-4 (FERM BP-1131, IFO 14483) or 22-3 (FERM BP-1133, IFO 14484).

4. A process according to claim 1, wherein the bacterium is *Pseudogluconobacter saccharoketogenes* TH14-86 (FERM BP-1128, IFO 14466).

5. A process according to claim 1, wherein the compound is D-glucose.

6. A process according to claim 1, wherein the compound is D-gluconic acid.

7. A process according to claim 1, wherein the compound is used in a concentration of 1–30% (w/v) based on the medium, when contacting the compound with the bacterium.

8. A process according to claim 7, wherein the concentration is 5–20% (w/v) based on the medium.

* * * * *